United States Patent [19]

Milner

[11] Patent Number: 5,032,501

[45] Date of Patent: Jul. 16, 1991

[54] DNA PROBES TO VNTR LOCI

[75] Inventor: Eric C. B. Milner, Seattle, Wash.

[73] Assignee: Virginia Mason Research Center, Seattle, Wash.

[21] Appl. No.: 310,140

[22] Filed: Feb. 10, 1989

[51] Int. Cl.$^5$ .................... C12Q 1/68; C07H 15/12; C12N 15/00
[52] U.S. Cl. ........................................ 435/6; 536/27; 935/77; 935/78
[58] Field of Search ................ 435/6; 536/27; 935/77, 935/78

[56] References Cited

PUBLICATIONS

Maniatis et al., Molecular Cloning-a Laboratory Manual, 1982, Cold Spring Harbor Laboratory, pp. 382–389.
Lathrop et al., Am. J. Human Genetics, vol. 37, pp. 482–498.

*Primary Examiner*—Robert A. Wax
*Assistant Examiner*—Mindy B. Fleisher
*Attorney, Agent, or Firm*—Seed and Berry

[57] ABSTRACT

DNA probes capable of specifically hybridizing to DNA from an allele of the locus D4S139 are disclosed. The probes may be used within a method for determining the existence of a biological relationship, a method for the identification of the source of a bio-forensic specimen, or within a method for the identification of the haplotype of the source of a biological sample.

31 Claims, 5 Drawing Sheets

VNTR Probe

Y Chromosome Probe

DNA PROBES TO VNTR LOCI

TECHNICAL FIELD

The present invention generally relates to the use of DNA probes specific for the human VNTR locus, D4S139. The present invention has applications in forensic typing, parenthood testing, genome mapping and in the determination of disease predisposition.

BACKGROUND OF THE INVENTION

Traditional protein methods for the typing of blood and semen are based on allelic differences in proteins (Divall, *Electrophoresis* 6:249–258, 1985; Sensabaugh, *Current Topics in Biological and Medical Research* 6:247–282, Alan R. Liss, New York, 1982). Enzyme and antigenic variants which have been examined in blood include adenylate deaminase, adenylate kinase, carbonic anhydrase I, erythrocyte acid phosphatase, esterase D, glyoxylase I, hemoglobin, peptidase A, phosphoglucomutase, and Gm, Lewis, and Rh antigens. In paternity testing, typing of the HLA antigens is commonly used (Terasaki, *J. Family Law* 16:543, 1977–1978). The analysis of proteins in semen involves the characterization of the following systems: ABO blood group, phosphoglucomutase, glyoxylate, peptidase A, and the Lewis antigens. While these traditional methods, when used in combination, can exclude up to 99% of the general population as the source of a biological sample, these methods do not allow the unequivocal identification of a particular individual as the source of the biological sample or as the first degree relation (Gaensslen, *Sourcebook in Forensic Serology, Immunology and Biochemistry.* U.S. Government Printing Office, Washington, D.C. 1983). Potential problems with protein typing include changes in electrophoretic mobility with aging of the sample, and possible cross-reactivities and artifacts due to other materials in the evidential sample (wool, for instance).

Polymorphic regions of human DNA are also being used as a basis for the identification of human bio-forensic evidence specimens and in the establishment of both first degree and higher order biological family relationships. The technique for the examination of polymorphic DNA regions is called "DNA fingerprinting," "DNA profiling," or "DNA typing," and has clearly become the method of choice in these areas. DNA typing with appropriate probes allows the identification of genotypes that would not be expected to be duplicated within the entire human population.

DNA typing is based on the detection of intergenic regions of nuclear DNA that are composed of variable numbers of tandem repeats (VNTRs). VNTRs are also known as "hypervariable minisatellite restriction fragment length polymorphisms." These loci are found on a number of different chromosomes, which makes the appearance of a given VNTR allele statistically independent of most others. The large number of alleles (up to 70–80 or more) that can be found at many of the VNTR loci, combined with the high level of heterozygosity (greater than 88%), are features that make VNTRs useful for identification purposes (Nakamura et al., *Science* 235:1616–1622, 1987).

For example, Jeffreys et al. have described the use of three VNTR-specific probes for DNA fingerprinting (*Nature* 316:76–80, 1985). The probes in the Jeffreys et al. study detected upwards of 15 hybridizing bands per person. Although the hybridization patterns were complex, this work led to results which convinced the British immigration authorities that a man desiring entry into the country was, in fact, the son of a (female) citizen (Jeffreys et al. *Nature* 317:818–819, 1985).

DNA fingerprinting using the DNA-print TM system (Lifecodes Corporation, Elmsford, N.Y.) with probes recognizing four different VNTR loci has also been used to establish paternity with a probability of greater than 99% (Baird et al., in *Advances in Forensic Haemogenetics* 2, Springer Verlag, New York, 1987).

Forensic applications of DNA fingerprinting have also been described. Gill et al. (*Nature* 318:577–579, 1985), successfully isolated DNA suitable for fingerprinting from such specimens as vaginal swabs, 4-yr-old dried bloodstains and semen stains on cloth. In another report on the DNA-print TM system, which allows discrimination at levels greater than in $10^8$ individuals, the probes were used to establish that human tissue found on a car apparently involved in a homicide was likely to be from the offspring of the parents of the car's registered owner, with a 1 in 160,000 chance that the tissue was derived from an unrelated individual (Baird et al., in *Adv. Forensic Haemooenetics* 2, Springer-Verlag, New York, 1987).

DNA typing presents obvious advantages over protein typing methodologies, including less interference from other materials in the evidential samples, and greater stability of DNA as compared to protein in dried samples. DNA typing also presents the possibility for re-use of the same DNA gel or blot for multiple sequential hybridizations. However, due to a lack of sensitivity of the probes, and the relatively small size of the useful restriction fragments identifying other VNTR loci, the true potential for the commercial application of such probes has not yet been realized.

The present invention provides a novel group of DNA probes that recognize the human VNTR locus, D4S139, a highly polymorphic region. These probes overcome the disadvantages briefly discussed above, while providing other related advantages.

DISCLOSURE OF THE INVENTION

Briefly stated, the present invention provides DNA probes capable of specifically hybridizing to DNA from an allele of the D4S139 locus, and methods for the use of those DNA probes in forensic investigations, in questions of paternity or other biological relationships, genome mapping, or in the determination of the predisposition to a genetic disorder. Furthermore, the DNA probes and methods of the present invention may be used as an alternative to classic fingerprint identification methods.

In one aspect of the present invention, a method for determining the existence of a biological relationship is provided, comprising the steps of (a) digesting DNA from a biological sample taken from an individual whose biological relationship is questioned and DNA from a biological sample taken from a putative biological relation in parallel with a restriction endonuclease, (b) size-fractionating the restriction endonuclease-digested DNA fragments; (c) hybridizing the DNA fragments with a labeled DNA probe capable of specifically hybridizing to DNA from alleles of the D4S139 locus; (d) separating the nonhybridized labeled probe; (e) detecting bound labeled probe; and (f) analyzing the identity or partial identity of the hybridization patterns of the individual and the putative biological relation.

Within another aspect of the present invention, a method for the identification of the source of a bio-forensic specimen is disclosed. The method generally comprises the steps of (a) digesting DNA from a bio-forensic specimen and DNA from a biological sample taken from a putative source of the bio-forensic specimen in parallel with a restriction endonuclease; (b) size-fractionating the restriction endonuclease-digested DNA fragments; (c) hybridizing the DNA fragments with a labeled DNA probe capable of specifically hybridizing to DNA from alleles of the D4S139 locus; (d) separating nonhybridized labeled probe; (e) detecting bound labeled probe; and (f) determining whether the putative source is the actual source of the bio-forensic specimen.

Within an additional aspect of the present invention, a method for the identification of the haplotype of the source of a biological sample is disclosed. The method generally comprises the steps of (a) digesting DNA from a biological sample with a restriction endonuclease; (b) size-fractionating the restriction endonuclease-digested DNA fragments; (c) hybridizing the DNA fragments with a labeled probe capable of specifically hybridizing to DNA from alleles of the D4S139 locus; (d) separating nonhybridized labeled probe; (e) detecting bound labeled probe; and (f) determining the haplotype at the D4S139 locus of the DNA in the biological sample. This embodiment of the present invention is also useful where a particular D4S139 haplotype has been associated with predisposition to a genetic disease.

Within the methods briefly described above, the DNA probes capable of specifically hybridizing to the D4S139 locus may be derived from human genomic clones or the DNA probe may be an oligonucleotide probe. Within one embodiment of this invention, the DNA probe is a 21 bp oligonucleotide comprising the sequence 5'-GCCGTGTCCTCGGCTCTCAGG-3'. Within a preferred embodiment, the DNA probe is a 4.5 kbp fragment of human DNA from the D4S139 locus.

These and other aspects of the present invention will become evident upon reference to the following detailed description and attached drawings.

BEST MODE FOR CARRYING OUT THE INVENTION

As noted above, the present invention is directed toward the use of DNA probes that specifically recognize the human VNTR locus, D4S139. Use of D4S139-specific probes presents a number of advantages over other available VNTR probes. Since D4S139 probes function as single locus probes when used under conditions of moderate to high stringency, the hybridization banding pattern is more simple than that observed with other probes which recognize multiple loci. As a result, it is possible to analyze mixed samples with the probes of the present invention. Such mixed samples may occur in mixed bloodstains or in vaginally derived samples from a rape victim. Through use of probes to the D4S139 locus, the technician can readily recognize and adapt to experimental difficulties, such as incomplete restriction endonuclease digestion or partially degraded DNA samples. A further advantage to the single locus D4S139 system is that under the preferred high stringency conditions of the hybridizations, there is less cross-hybridization with DNA from other species which might be present as a contaminant in the sample or be mixed with the evidential sample.

The D4S139 locus is on the long arm of human chromosome 4 near the telomere of 14q, 15-20 cM (centimorgans) from the most telomeric known marker, L231, with a LOD score greater than 3.00. The D4S139 locus was mapped to human chromosome 4 through linkage analysis using known chromosome 4 markers. This locus is capable of specifically hybridizing under conditions of high stringency (0.1 x SSC, 1% SDS, 65° C.) with representative probes, such as oligonucleotide H30 or the 4.5 kbp D4S139 probe. Associated with the actual repetitive DNA sequences at the D4S139 locus, there is additional flanking DNA. Probes useful for identifying alleles of the D4S139 locus and contemplated within the present invention may be derived from the tandemly repeated DNA sequences or from DNA flanking those repeated sequences. The actual extent of DNA flanking the repeated DNA sequences depends on the restriction enzyme used for defining the D4S139 allele, as is evident to the skilled artisan.

Oligonucleotide H30, a probe useful within the methods of the present invention, is a 21 bp oligonucleotide which contains the sequence 5'-GCCGTGTCCTCGGCTCTCAGG-3'. This oligonucleotide may be excised from a plasmid bearing the sequence, such as 30pl (Schroeder et al., Science 238:791-793, 1987), or it may be chemically synthesized according to methods well known in the art.

As noted above, another representative probe of the present invention, the 4.5 kbp D4S139 probe, functions as a single locus probe under conditions of high stringency (0.1×SSC, 1% SDS, 65° C.). The 4.5 kbp D4S139 probe was isolated as a Sau3A fragment from a human genomic library constructed in lambda phage EMBL using the cell line CRI as the source of the DNA.

In addition to the representative probes described above, it will be evident to one skilled in the art, given the teachings provided herein, that other probes may be generated for use within the present invention. Briefly, one can specifically hybridize a D4S139-specific probe to size fractionated, restriction endonuclease-digested human DNA to identify fragment sizes carrying D4S139 alleles. Appropriately size-fractionated DNA is then prepared for ligation into a suitable vector. It will be understood in the art that the step of size-fractionation is preferable, but not essential in the cloning of D4S139 alleles. Clones are screened with a D4S139-specific probe, such as the probes described above, and positive clones are further characterrized. This procedure allows the generation of additional D4S139-specific probes from alleles other than that which gave rise to the 4.5 kbp D4S139 fragment described above.

Figure 4:
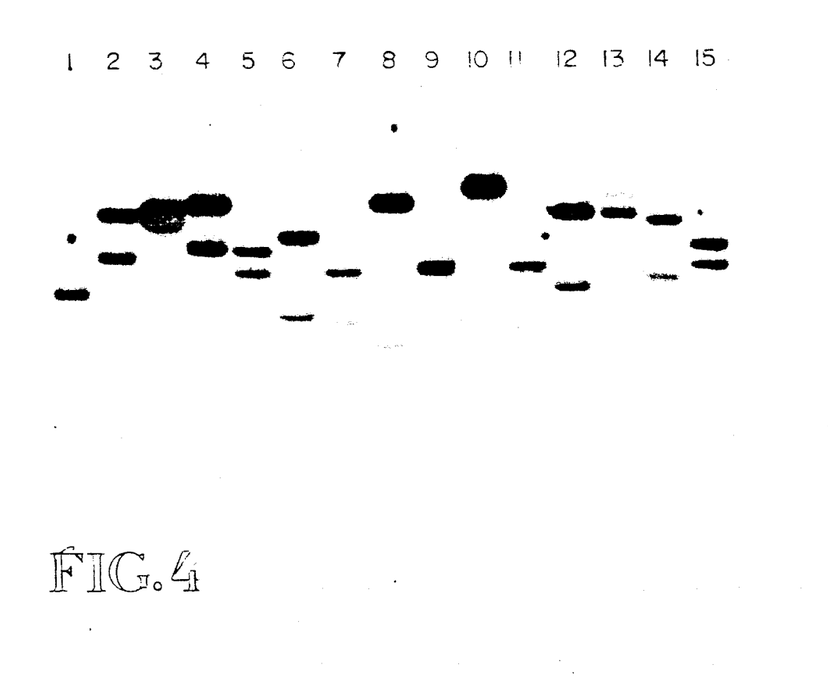
FIG. 4 illustrates the patterns of hybridization to the H30 oligonucleotide probe for TaqI-digested DNA samples from 15 unrelated individuals.

The high degree of polymorphism associated with the D4S139 locus is illustrated through stringent hybridization to human genomic DNAs digested with the restriction enzyme TaoI using the oligonucleotide H30 probe described above. FIG. 4, which shows the patterns of oligonucleotide H30-specific hybridization for TacI-digested DNAs from 15 unrelated individuals, illustrates the existence of at least 20 alleles of the D4S139 locus, with D4S139-related bands ranging in size from about 5 kbp to about 23 kbp, with an average size around 9 kbp. Generally, two bands per DNA isolate were observed. Thus, individuals chosen at random from the general population are highly heterozygous for the D4S139 locus, and there is a large amount of diversity in the sizes of the D4S139-hybridizing bands. Therefore, the D4S139-specific probes of the present invention allow the use of DNA typing for the identification of individuals. Similar results were obtained using another representative probe, the 4.5 kbp D4S139 fragment. In addition to the use of TaoI, there was also a simple pattern of diverse-sized D4S139-hybridizing bands when the DNA samples were digested with other restriction enzymes, such as EcoRI, HindIII, BqlII, BamHI, PstI, AluI, HinfI, HaeIII, RsaI and XbaI.

As noted above, the probes described herein may be utilized in the identification of the source of a bio-forensic specimen, determining the existence of a biological relationship, genome mapping and in the determination of disease predisposition.

Within the identification of the source of a bio-forensic specimen, the probes of the present invention are used to visualize specific D4S139 alleles in DNA derived from bio-forensic specimens. Briefly, DNA from a sample is preferably first extracted prior to digestion. The DNA is then digested with a restriction endonuclease, size-fractionated by agarose gel electrophoresis, and usually transferred to a substrate, such as nylon or nitrocellulose, for subsequent hybridization. Labeled D4S139 probes are then hybridized, preferably under conditions of high stringency. Matching D4S139-hybridizing bands in DNA fragments prepared from the specimen and from a known individual give presumptive identification of the ultimate source of the evidential sample.

Bio-forensic specimens containing human DNA may be derived from a crime victim or from a member of the family of a crime victim or a suspect. In addition, the specimen may be a sample from the scene of a crime or accident, or a suspected crime or accident. Bio-forensic specimens include, but are not limited to, blood, dried blood, dried bloodstains, semen, dried semen, dried semen stains, oral swabs, vaginal swabs, vaginal fluids, dried vaginal fluid stains, or other body fluids and body fluid stains, seminal fluid, dried seminal fluid, hair, hair roots, and tissue samples from the human body. Specimens may be postmortem, premortem, prenatal or neonatal.

Identifying the source of a bio-forensic specimen utilizing the probes of the present invention is useful, for example, in confirming that a bloodstain on a suspect's clothing was derived from the crime victim, demonstrating that DNA in a vaginal sample from a rape victim was derived from a particular suspect, and in establishing the identity of a crime victim by showing genetic relatedness to the persons believed to be the parents (or other familial or biological relatives) of the crime victim.

Figure 5A:
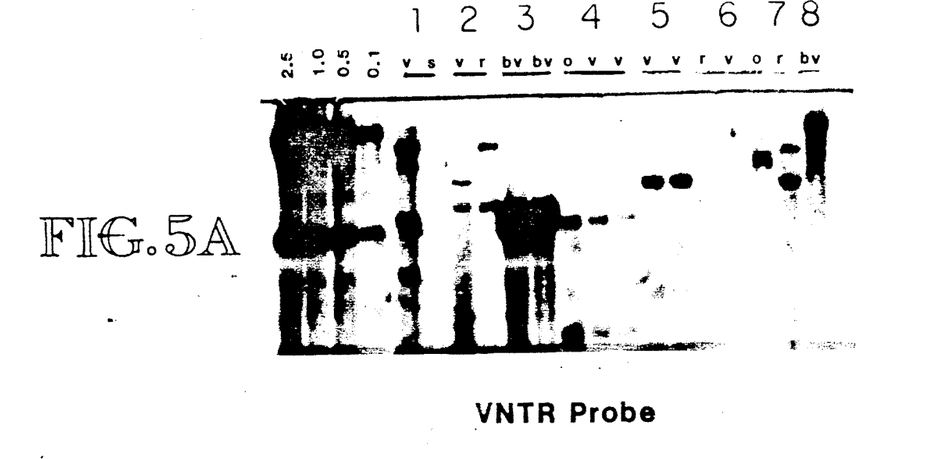
FIG. 5 illustrates the hybridization of the 4.5 kpb D4S139 probe to HinfI-digested DNA obtained from discarded sexual assault evidence swabs. Standard human male DNA, numbered in micrograms of DNA, was loaded in the leftmost 4 lanes. The sets of lanes numbered 1-8 contain DNA obtained from a set of swabs, each set being related to a particular case. The letters refer to the anatomical source of the swab: v, vaginal; s, skin; r, rectal; by, bloody vaginal; o, oral. Panel A illustrates the results of hybridization using the 4.5 kbp D4S139 fragment as probe. Panel B illustrates the results of hybridization with a Y chromosome-specific probe without intermediate stripping of the blot. The arrowhead denotes the position of the male-specific band.
Figure 5B:
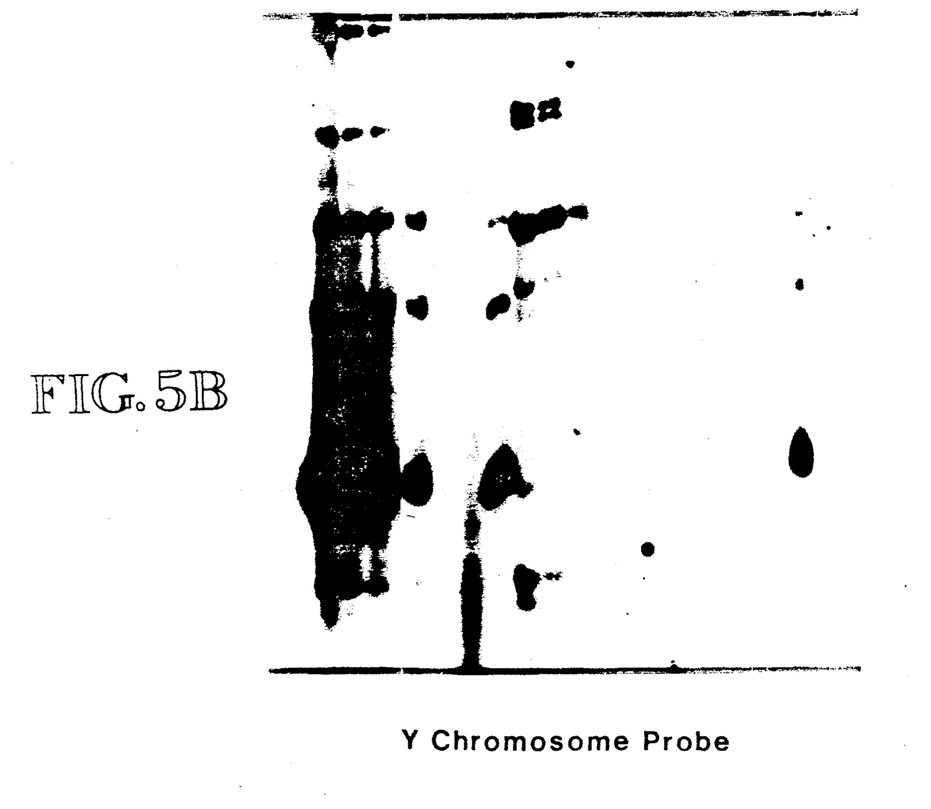

The usefulness of a DNA probe specific for the D4S139 locus within forensic typing is illustrated in FIG. 5. Briefly, DNA samples were isolated from (discarded) rape evidence swabs. Evidence swabs (including vaginal, rectal, oral, skin and bloody vaginal) from 8 sexual assault cases were analyzed, along with control male DNA. DNA samples were digested with HinfI, size-fractionated by agarose gel electrophoresis and hybridized with the 4.5 kbp D4S139 fragment as a probe, as shown in FIG. 5A. The blot was subsequently hybridized, without intermediate stripping of the D4S139 probe, to a Y chromosome-specific probe, as shown in FIG. 5B. The position of the male-specific band is marked with an arrowhead. The DNA typing evidence of case 2 shows that DNA was present in both vaginal and rectal samples, with male DNA present only in the rectal swab. Similarly, a sample from case 8 also shows the presence of male DNA. In case 2 (Panel A) the victim and assailant share a lower molecular weight D4S139 allele. By sequentially probing with the Y chromosome-specific probe, it was confirmed that male DNA was present. In other applications, it may also be useful to use sequential hybridizations, with or without the step of intermediate stripping of the blot, with single locus probes specific for additional VNTR loci. It is preferred to use combinations of probes when it is desired that an individual or a specimen source be unequivocally identified.

Within biological or familial relationship testing, the probes of the present invention are used to visualize the D4S139 alleles of an individual and his or her putative biological relative, so that familial relationships may be confirmed. Briefly, within a preferred embodiment of the present invention, DNA is prepared from a biological sample, such as blood or tissue sample, from the individual whose biological relationship is questioned in parallel with DNA from a known parent and/or a putative parent (or other biological relative). Commonly, peripheral blood samples are used as the source of DNA. DNA fragments are digested with restriction endonucleases, size-fractionated by agarose gel electrophoresis and transferred to a substrate, such as nylon or nitrocellulose, for hybridization to a labeled probe, preferably under conditions of high stringency. Because there is Mendelian inheritance of D4S139 alleles, one band of the individual will match with one band of the known parent. If a band of the alleged parent matches the second band of the individual, then there is presumptive evidence that the alleged parent is also a biological parent to the individual. If the DNA of the alleged parent shares no D4S139-specific bands, it is almost conclusive that there is no such biological relationship.

Figure 1:
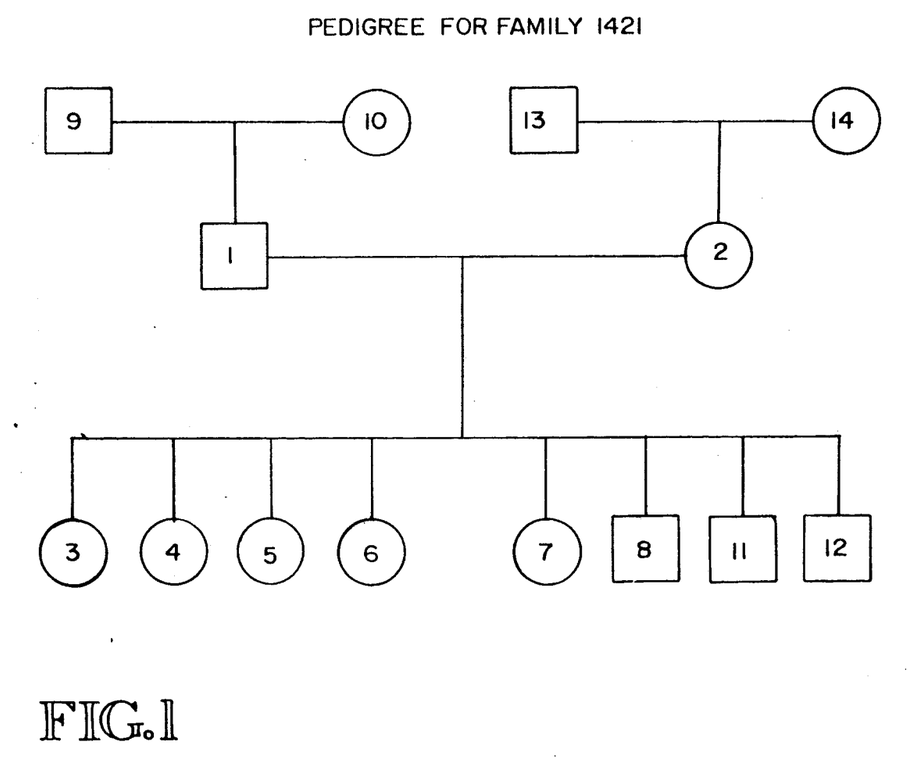
FIG. 1 depicts the pedigree of a three-generation family (1421) whose members, DNA fragments were analyzed by hybridization to the D4S139 4.5 kbp probe, as shown in FIG. 2. Males are represented by squares and females are represented by circles.
Figure 2:
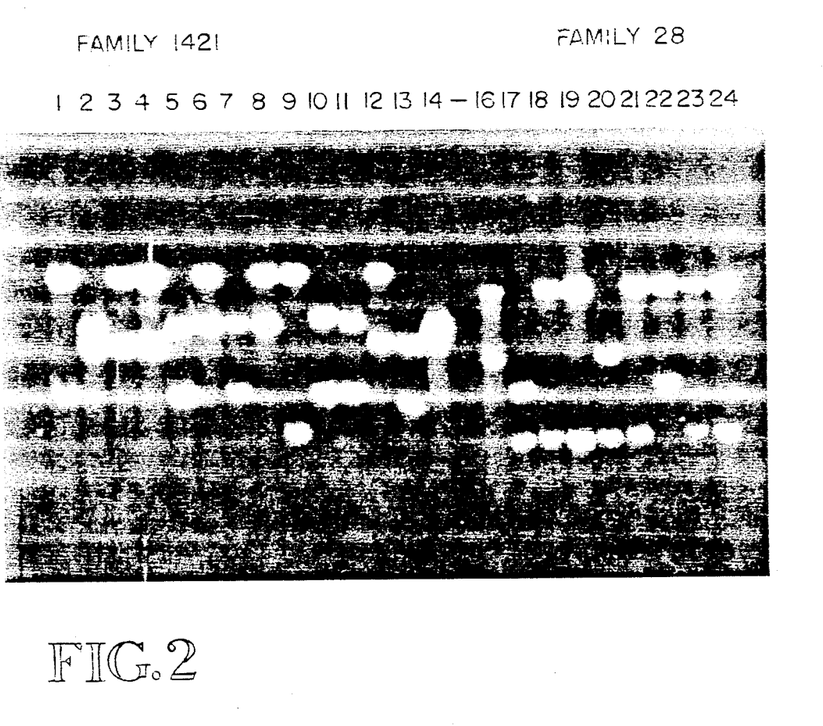
FIG. 2 illustrates the patterns of hybridization to the 4.5 kbp D4S139 probe to TaqI-digested DNA samples prepared from members of the family (1421) with the pedigree shown in FIG. 1. The DNA samples in lane numbers 1-14 correspond to the numbers given to the family members in FIG. 1. Lanes 16-24 contain DNA samples from a two generation family (28). Lanes 16 and 17 contain DNA from the parents and lanes 18-24 contain DNA from each of 7 offspring.

The Mendelian inheritance of D4S139 alleles is illustrated in FIG. 1, which depicts the pedigree of a representative three generation family (1421), and FIG. 2, which illustrates the D4S139-specific hybridization patterns for members of that family. Lanes 1 and 2 contain DNA from the father and mother, respectively (the second generation), and lanes 3-8 and 11-12 contain DNA from their offspring, i.e. the third generation. The first generation is represented in lanes 9 and 10, containing DNA of the paternal grandfather and grandmother, and in lanes 13 and 14, containing DNA from the maternal grandfather and grandmother, respectively. The banding patterns reflect the co-dominant segregation and the Mendelian inheritance of the D4S139 locus. One copy of chromosome 4 is inherited from each parent; therefore, a child will inherit one allele of the D4S139 locus from each parent. As a result, if the D4S139 alleles of two putative biological relatives are different, the parentage of a child can be confirmed using D4S139 DNA typing. As described herein, higher confidence levels for estimating biological familial relationships may be obtained through the use of other single locus VNTR probes in combination with the D4S139-related probes.

The haplotype of the source of a biological sample may also be determined using the methodology described herein. One application of such a haplotype determination is in identifying individuals that are predisposed to a particular genetic disease, when the inheritance of that genetic disease is associated with a particular allele of the D4S139 locus. Suitable biological samples in this regard include blood, tissue and cells. Prenatal, neonatal, post mortem and other samples may be used in this embodiment of the invention.

Within all of the methods envisioned by the present invention, it may be preferable to use the probes described herein in conjunction with other single locus VNTR probes in order to increase the confidence level of the experimental conclusions. Other single locus VNTR probes, the use of which is contemplated in conjunction with the D4S139-related probes of the present invention include, but are not limited to, pYNH24, pCMLJ14, and pCMM101, which are available from the American Type Culture Collection (ATCC). In addition, probes CRI-PAT-pL336 and CRI-PAT-pL335-8 may be obtained from Collaborative Research, Inc. (Bedford, Mass.).

Within all of the methods envisioned by the present invention, it may be preferable to analyze DNA from biological samples or bio-forensic evidence specimens without carrying out a DNA isolation procedure. It is known in the art, for example, that cells may be lysed, and the DNA released therefrom digested with restriction enzymes.

The following examples are offered by way of illustration, and not by way of limitation.

EXAMPLES

Enzymes are obtained from commercial sources, and are used according to the vendors, recommendations or other variations well known in the art. Suitable reagents, buffers and culture conditions are also known in the art. References containing standard molecular biological procedures include T. Maniatis et al., *Molecular Cloning*, Cold Spring Harbor Laboratory, Cold Spring Harbor, N.Y., 1982; Ausabel et al., *Current Protocols in Molecular Biology*, John Wiley & Sons, New York, 1987; R. Wu et al. (eds.), *Meth. Enzymol.* 100 and 101, 1983; L. Grossman and K. Moldave (eds.), *Meth. Enzymol.* 65, 1980; J. Miller (ed.), *Experiments in Molecular Genetics*, Cold Spring Harbor Laboratory, Cold Spring Harbor, N.Y., 1972; Old and Primrose, *Principles of Gene Manipulation*, University of California Press, Berkely, Calif.; R. Schlief and P. Wensink, *Practical Methods in Molecular Biology*, 1982; Glover (ed.), *DNA Cloning*, vols. I and II, Oxford Press, Oxford, UK, 1985; B. Hames and S. Higgins, *Nucleic Acid Hybridization*, IRL Press, Oxford, UK; Setlow and Hollaender, *Genetic Engineering: Principles and Methods*, vols. 1-4, Plenum Press, New York, all of which are expressly incorporated herein by reference. Chemical synthesis of DNA may be accomplished using well established procedures (i.e. Caruthers, in *Methodology of DNA and RNA Sequencing*, Weissman (ed.), Praeger Publishers, New York, 1983, or automated chemical synthesis can be performed using one of a number of commercially available machines. Abbreviations and nomenclature, where employed, are deemed standard in the field and commonly used in professional journals such as those cited herein.

DNA preparation, restriction endonuclease digestion, electrophoresis of DNA digests, transfer to nitrocellulose filters, and probe hybridization were performed according to standard protocols unless otherwise stated.

EXAMPLE 1

Genomic Cloning of the D4S139 Locus

The synthetic oligonucleotide H30 corresponds to a sequence extending from the third nucleotide of codon 82b through the second nucleotide of codon 88 of the $V_H3$ cDNA clone 30pl (H.W. Schroeder et al., *Science* 238:791, 1987). The 30pl cDNA clone represents a single member of the $V_H3$ gene family. The numbering is according to E.A. Kabat et al. (*Sequences of Proteins of Immunological Interest*, fourth edition, Dept. of Health and Human Services, Government Printing Office, Washington D.C., 1987). The sequence of this oligonucleotide is 5'-GCCGTGTCCTCGGCTCTCAGG-3'. For use in hybridization experiments, oligonucleotides are end-labeled using T-4 polynucleotide kinase in the recommended buffer.

Within this example, the source of a human genomic DNA fragment carrying the D4S139 locus was DNA from cell line CRI. This DNA was digested to completion with EcoRI and size fractionated on a 10 to 40% sucrose gradient. Following centrifugation, 1 ml fractions were collected from the bottom of the tube, and individual aliquots were analyzed by agarose gel electrophoresis and hybridization to the H30 oligonucleotide probe.

Hybridization of labeled oligonucleotide probes to genomic DNA in dried agarose gels was performed as described by Holbeck et al. (*Immunogenetics* 24:251, 1985) and Nepom et al. (*The Lancet* 11:1002, 1986). Final stringencies were obtained by washing in a solution containing tetramethyl ammonium chloride (TMACl, Aldrich) as described by W.I. Wood et al. (*Proc. Natl. Acad. Sci. USA* 82:1585, 1985). Briefly, digested DNA (10–15 μg/lane) was size-fractionated by electrophoresis in 1% agarose gels. DNA molecules within the gels were denatured 1–1.5 hours in 0.5M NaOH, 1.5M NaCl. Gels were then neutralized for 1–1.5 hours in Tris-HCl pH 7.0, 3M NaCl followed by a 10 min. wash in distilled water. Gels were dried under vacuum for 1.5 hrs. at 70° C. Filter paper backing was removed by soaking in water for 2 min. Gels were prehybridized in 6X NET (lX NET =0.1M NaCl, 0.03M Tris HCl pH 8.0, 1 mM EDTA) containing 250 μg/ml tRNA, at 57° C. for 1.5–3 hr. Gels were hybridized at 57° C. for 3–4 hr. with oligonucleotide probes end-labeled to a specific activity of approximately $1 \times 10^9$ cpm/μg at a concentration of $>3 \times 10^6$ cpm/ml in a solution containing 6X NET, 5X Denhardt's, 0.1% SDS, 0.05% NP40, 10% dextran sulfate and 250 μg/ml tRNA. Following hybridization, gels were washed three times at 43° C. in 5×SSC, 0.5% SDS, followed by two washes in 3.2M TMACl, 0.5% SDS for a minimum of 30 min. per wash at 61° C.

Fractions containing DNA which hybridized to the probe were pooled and ligated into lambda phage EMBL4 arms (Stratagene, San Diego, Calif.). Approximately 95,000 plaques were screened with the H30 oligonucleotide probe and 20 positive clones were picked on the basis of hybridization at low stringency to the H30 probe. Four of these clones were plaque-purified, and of these, two were found to hybridize to the H30 oligonucleotide probe at high stringency, indicating complete homology. One of these was selected for further experimentation. The selected lambda clone was digested to completion with Sau3A, and a 4.5 kbp band was isolated from an agarose gel and subcloned into the BamHI site of the plasmid bluescript (Stratagene, San Diego, Calif.). The resulting plasmid was designated pH30.

For hybridization to genomic blots, in order to determine polymorphism at the D4S139 locus, a D4S139-related fragment was cut out from pH30 with the enzymes EcoRI and HindIII and the purified fragment was labeled with $^{32}$P-α-dCTP by the random primer method described by Feinberg et al. (*Anal. Biochem.* 132:6, 1983). Screening of restriction endonuclease-digested genomic DNA with this probe revealed more than 20 alleles ranging in size from about 5 kbp to about 23 kbp, with an average of approximately 9 kbp, as shown in FIG. 4.

EXAMPLE 2

Chromosomal mapping of D4S139

A panel of 14 mouse/human somatic hybrid cell lines (obtained from Dr. D. Provtecheva, Yale University), each containing a subset of the human chromosome complement were hybridized with the H30 oligonucleotide probe. The pattern of hybridization to this probe unambiguously mapped the D4S139 locus to human chromosome 4.

Linkage analysis with known chromosome 4 markers using published techniques (Lathrop et al., *Am. J. Human Genetics* 37:482–498, 1985) placed the D4S139 locus near the telomere of 14q, 15–20 cm from the most telomeric known marker (L231), with a LOD score of greater than 3.0.

EXAMPLE 3

Sequence Determination of the 4.5 kbp D4S139 Fragment

An approximately 4.5 kbp insert of pH30 was subcloned into a pUC vector (J. Viera- and J. Messing, *Gene* 19:259, 1982). Clones containing overlapping deletions for sequencing are constructed by the method of R. Dale et al. (*Plasmid* 13:31, 1985). The DNA sequence of the human DNA insert is subsequently determined using the chemical cleavage technique of A. Maxam and W. Gilbert (*Meth. Enzymol.* 65:499, 1980), and the chain termination method of F. Sanger et al. (*J. Mol Biol.* 143:161, 1980).

EXAMPLE 4

Generation of Additional D4S139-Specific Probes

One skilled in the art can isolate additional genomic DNA fragments and other oligonucleotide probes to be used as specific hybridization probes for the D4S139 locus by following the procedures briefly outlined in either A or B below.

A. Using the sequence for the 4.5 kbp D4S139 fragment, it would be evident to the skilled artisan how to choose other oligonucleotide sequences, preferably about 14–25 nucleotides in length, for use as probes specific for the D4S139 locus. Briefly, a sequence is chosen, compared with known sequences in available databases, and those sequences which appear to be unique are tested, preferably under stringent hybridization conditions, for the ability to serve as single locus probes for the D4S139 locus.

B. Other genomic DNA fragments, from the same or a different source than as described above, can also serve as specific hybridization probes for the D4S139 locus. Briefly, human genomic DNA is prepared and digested with a restriction endonuclease. After size separation by agarose gel electrophoresis, the size-separated DNA fragments are probed, preferably under stringent conditions, with labeled oligonucleotide probe H30. The sizes of those bands specifically hybridizing to the probe are noted. Additional genomic DNA is digested with the same restriction endonuclease and size-fractionated, for example, by ultracentrifugation through a 10 to 40% sucrose gradient. Aliquots of the size-fractionated DNA are electrophoresed and hybridized to the H30 probe to confirm that D4S139 fragments are present. Positive fractions are prepared for cloning and screening essentially as described above. Confirmed positive clones are purified and the D4S139 fragments are labeled for testing in hybridization experiments. DNA fragments which specifically hybridize to the D4S139 locus under stringent hybridization conditions are retained for further experimentation.

EXAMPLE 5

Biological Relationship Testing

In cases where it is questioned whether a particular individual is the biological parent of a child, it is possible to determine with a high degree of certainty whether the individual is indeed a parent. Peripheral blood samples are taken from the child and from the individual in question. If possible, it is preferable to obtain and analyze the DNA from a known parent as well. High molecular weight DNA is extracted from 1 ml of each blood sample as described by Baird et al. (*Am. J. Human Genetics* 39:489–501, 1986). Each isolated DNA sample is then digested with a restriction endonuclease, such as TaqI, and size-fractionated by agarose gel electrophoresis using standard techniques. After denaturation of the DNA, the DNA is transferred to a solid support for hybridization to a labeled probe specific for the D4S139 locus, such as oligonucleotide H30 or the 4.5 kbp D4S139 fragment. When the size-fractionated DNA is bound to a substrate or support, such as nylon or a nitrocellulose filter, best results are obtained using the 4.5 kbp D4S139 fragment or a probe of a similar size. As noted above, it is preferable when using oligonucleotide probes to perform hybridization to DNA molecules in agarose gels. When the hybridized bands are visualized, one observes a band in the child's DNA co-migrating with a band of the known parent, and determines whether there is a match between the child and the putative parent. If there is a match with the putative parent, it is likely that the putative parent is a biological parent of the child. If there is no match between the hybridization patterns of the child and the putative parent, one can conclude that it is empirically likely that the child and the putative parent are unrelated. The probability of parenthood is determined in part from a knowledge of the frequency of the alleles within the general population. In this regard, it is preferable to use the D4S139 probes of the present invention in conjunction with other single locus probes to VNTR loci in order to increase the confidence of the experimental conclusions.

The applicability of DNA typing using a D4S139 single locus probe has been demonstrated in hybridization studies of related and unrelated individuals. Briefly, the 4.5 kbp D4S139 probe was hybridized under stringent conditions to TaoI-digested DNA derived from eighteen three-generation families and six two-generation families. The hybridization banding patterns for representative two- and three-generation families are illustrated in FIG. 2.

Figure 3:
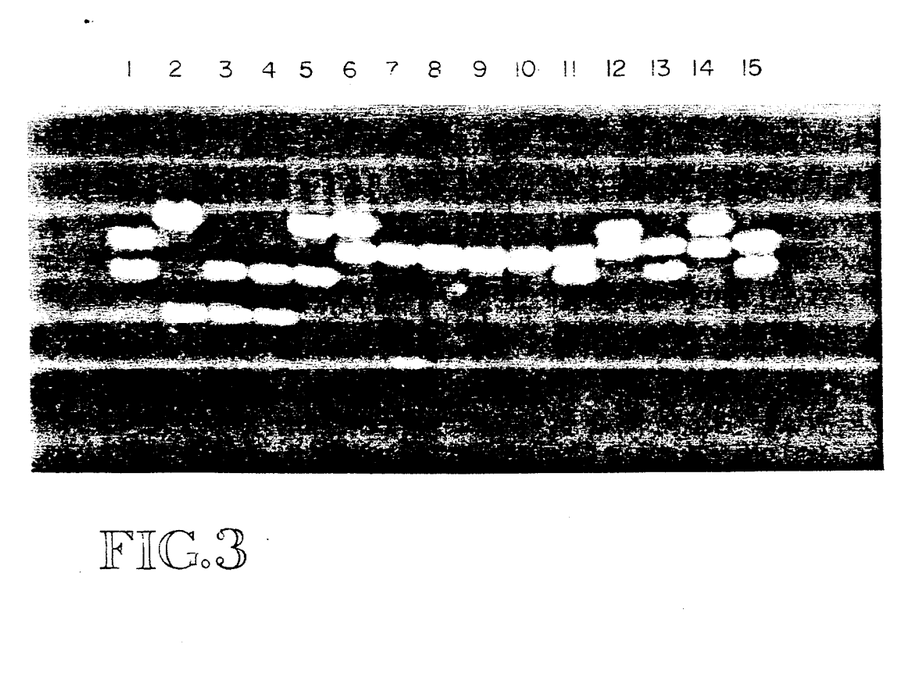
FIG. 3 illustrates the patterns of hybridization of the H30 probe to TaoI-digested DNA fragments prepared from three, two generation families. Lanes 1 and 2 contain DNA from the father and mother, respectively, and lanes 3, 4 and 5 contain DNA from each of the three offspring. Lanes 6-10 and 11-15 depict the analysis of two additional families. The same loading pattern is used for each family.

FIG. 3 illustrates the distribution of D4S139 alleles in three additional two-generation familes. Within FIG. 3, the pattern of father, mother, and three children is repeated three times. DNA samples derived from the individuals depicted in the patterns of FIG. 3 were prepared and digested with TaqI. After size-fractionation by agarose gel electrophoresis, hybridization in a dried agarose gel, under stringent conditions, was accomplished using the H30 oligonucleotide as the labeled probe for hybridization. Alternatively, using the 4.5 kbp D4S139 probe, hybridization may be conducted under stringent conditions, and with the size-fractionated DNA fragments bound to a solid support. Similar results were obtained using other restriction endonuclease digests and using the 4.5 kbp D4S139 fragment as a probe. The banding patterns reflect the Mendelian inheritance of the D4S139 locus. One of each of the two bands in an individual's banding pattern is identical with one of the two bands from the banding pattern of each parent.

In contrast, FIG. 4 illustrates the hybridization banding patterns obtained when DNA samples were prepared and analyzed from 15 unrelated individuals. As described above, at least 20 different alleles of the D4S139 locus were observed, and there were no two identical banding patterns observed.

Thus, the observation of identical bands appearing in the DNA fragments of two individuals strongly suggests that a biological relationship exists.

EXAMPLE 6

Forensic typing

DNA can theoretically be isolated from any cell which contains a nucleus, and any evidential specimen which contains nucleated cells is a candidate for DNA typing. Bio-forensic evidence specimens include, but are not limited to, vaginal swabs obtained from the victims of sexual assualt, dried semen, bloodstains, and tissue (preferably frozen). Other bio-forensic evidence specimens include blood, dried blood, semen, seminal fluid, dried seminal fluid, vaginal fluid, oral swabs, hair and hair roots. Control samples may be obtained from freshly drawn EDTA anticoagulated blood. DNA typing can be performed with as little as 5 $\mu$l of blood, 1 $\mu$l of semen, a 1 cm bloodstain, or 1–5 hair roots. DNA in most such samples appears to be quite stable. For instance, high molecular weight DNA has been isolated from dried blood and semen stains up to five years old. Typeable sperm DNA can be obtained from a vaginal swab collected 12 hours or more after intercourse. Samples may be postmortem, premortem, prenatal or neonatal.

Specimen storage is often particularly important. Specimen samples should be kept free from moisture, since DNA generally degrades in a humid environment, and protected from sunlight. Specimens should be stored at 4° C. in the presence of a desiccant or frozen at −20° C. under non-frost free conditions.

The isolation of DNA from peripheral blood, vaginal swabs and lavage fluids, dried blood stains, and semen stains has been described by Kanter et al. (*J. Forensic Sciences* 31:403–408, 1986), Giusti et al. (*J. Forensic Sciences* 31:409–417, 1986) and Baird et al. (*Am. J. Human Genetics* 39;489–501). DNA may be similarly extracted from tissue samples after they have been minced.

The isolated DNA samples are digested with restriction endonucleases, size-separated by agarose gel electrophoresis, and analyzed by hybridization using a D4S139-specific probe, as described above. It is preferable to utilize a relatively large probe, for example, the 4.5 kbp D4S139 fragment, when the DNA is affixed to a substrate such as a nitrocellulose filter. As noted above, it is preferable, when using oligonucleotide probes, to perform hybridization in a dried agarose gel.

Analysis of DNA samples from evidence specimens in parallel with DNA samples from known sources or individuals by DNA typing with D4S139-specific probes allows the determination of the source of an evidence specimen. It is also understood that one can use the results of DNA typing of evidence specimens in conjunction with DNA typing done at other times, e.g., through the use of computer databases.

Within preferred methods of forensic testing and biological relationship testing, the following procedures are followed.

DNA may be prepared from 5–10ml EDTA anticoagulated whole blood, which may be stored 24 hours at room temperature or at 4° C. for up to one month. The expected yield is 100 to 200 micrograms of DNA.

After centrifugation of the blood, the buffy coat is removed to a 50 ml tube with a plastic transfer pipette. Red Cell Lysis Buffer (10 mM NaCl, 10 mM Tris 8, 1 mM EDTA 8) is added to 45 ml and mixed by inversion and is incubated 10 minutes room temperature. White cells are pelleted in a serological centrifuge. The supernatant is poured off and the pellet is resuspended in Red Cell Lysis Buffer. This step is repeated two or three times until supernatant is clear.

The white cell pellet is resuspended in 2ml TB-1 (100mM NaCl, 25 mM EDTA pH 8, 10mM Tris pH 8) with vortexing, and 0.1 ml TB-2 (10% SDS) is added with vortexing. 20 microliters TB-3 (proteinase K 10mg/ml) are added with vortexing. Samples are incubated 55° C. 4 hours to 3 days. At this point the specimen can be stored at −20° C., preferably under non-frost-free conditions.

DNA is purified by two organic extractions and precipitations. Phenol/chloroform reagent is added to the tube equal in volume to the sample volume and mixed by gentle inversion for 1 minute. The layers are separated by centrifugation in seroligical centrifuge at maximum rpm for 15 min. The bottom yellow layer is removed and discarded with eppendorf or pasteur pipette. DNA may be at the interface if highly concentrated in large scale preparations from whole blood or tissues, and will cause a disturbance at the interface if it is being drawn into the pipette. If this occurs, the sample is recentrifuged. If the problem persists, an additional 2 ml of TE is added to the sample and the extraction is repeated. An equal volume of chloroform reagent is added, the sample is mixed and centrifuged. The organic layer is removed and discarded. One-tenth volume of precipitation salts is added with thorough mixing by inversion. 2 to 3 volumes of −20° C. 95% alcohol are added with thorough mixing by inversion. The sample is placed at −20° C. for 30 min. Samples are centrifuged at 4 to 5000×G for 20 minutes or until a tight visible pellet appears. Alternatively, the DNA can be removed with the bent end of a pasteur pipette and placed in a microfuge tube, 1 ml ethanol added and the DNA pelleted in a microfuge. Supernatants are carefully removed. The pellets are washed twice with room temperature alcohol reagent by flowing approximately 500 microliters down the side of the tube opposite the pellet while holding at a 45° angle. The tube is rotated twice and the supernatant is removed. Pellets are dried with tubes inverted approximately two hours. Each DNA pellet is resuspended in 500 microliters sterile TE. Resuspension can be at 40° C. overnight or at 65° C. for one hour. Long term storage can be at −20° C. or lyophilized at room temperature, or samples may be stored at 4° C. for up to one month.

The procedure for the elution of blood and semen stains from cloth and swabs is described below.

A swab tip or an approximately 1 square centimeter blood or semen stain is placed in 0.5 microliter elution chamber. 300 microliters TB-1 (100 mM NaCl, 25 mM EDTA pH 8, 10 mM Tris pH 8) are added and incubated at room temperature 30 minutes with vortexing every 10 min. Aliquots may be withdrawn for acid phosphatase, P-30 or other determinations as required. 30 ul of TB-2 (10% SDS) are added, and the samples are reincubated at room temperature 30 minutes vortexing every 10 minutes. The elution chamber is placed in a centrifuge tube and centrifuged in a serological centrifuge. 5 ul of TB-3 (PK) and DTT to 39 mM are added, then incubated at 55° C. one hour to overnight. At this point the specimen can be stored at −20° C. The extraction procedure is repeated. DNA samples or digests are size-fractionated by electrophoresis on 1% agarose gels containing E buffer and ethidium bromide. Gels of about 50 ml in volume are electrophoresed at 50–80 VDC for 2-4 hours. Size standards (lambda HindIII molecular weight markers, 250 nanograms) are placed in the two outer lanes. Human DNA standards of known concentration, determined by fluorimetry (1 microliter=50 ng) are placed in selected gel lanes. Suggested loadings are 50, 100 and 500 ng. Comparison of the intensities of these lanes with each unknown gives a good approximation of the DNA concentration in the unknowns. Intensities are observed using a UV transilluminator. 5 microliters of eluate DNA or 1 to 5 microliters of blood DNA are mixed with loading dye prior to loading.

DNA of known concentration is digested with HinfI using the following procedure. A final DNA concentration of 100 nanograms/microliter is ideal, although higher concentrations can be used. Restriction enzyme is added at 2.5U/microgram of DNA to be digested in the appropriate buffer-spermidine-DNA mixture. Digestion mixtures are mixed thoroughly and centrifuged if necessary to bring all of the solution to the bottom of the tube, and incubated 2 hours at 37° C. Additional restriction enzyme is added at 2.5U/microgram of DNA and the digestion mixtures are reincubated at 37° C. 2 hours. At this point a 2.5 microliter (250 nanogram) sample can be electrophoresed on a 1% agarose gel to assess the completion of the restriction digest. Suitable molecular weight markers are lambda DNA digested with HindIII and phi X174 DNA digested with HaeIII. Additionally each sample can be analyzed by blotting to determine the presence of male DNA and microbial contamination.

A suitable gel loading pattern for a 25 lane gel is lanes 1-3, molecular weight marker DNAs; lanes 4-6, HinfI-digested control DNAs, 5 micrograms per lane; lanes 7-10, DNA samples to be analyzed, 3-6 micrograms per lane; lanes 11-13, molecular weight marker DNAs; lanes 14-23, DNA samples to be analyzed, 3-6 micrograms per lane; lanes 24-25, molecular weight marker DNAs.

A gel of about 350 ml volume is electrophoresed in E buffer at 20 V 30 minutes and then at 40 V until ⅓ of the dye front is off the gel, approximately 20 hours. The gel is photographed using the UV transilluminator as the illumination source.

In order to affix the DNA fragments to a substrate or membrane for hybridization, the following procedures are followed.

A blotting platform is constructed by placing two pipet racks in a pyrex baking dish to support a glass plate. 3 MM wicks are placed over the glass plate and thoroughly wetted with transfer solution (0.4M NaOH). Air pockets are removed and a stack of 10 sheets of 3 MM thoroughly wetted with transfer solution are added, and the air pockets are removed by rolling with a pipette without wrinkling the sheets of 3 MM. Transfer solution is added to the baking dish to a depth of approximately ¼". Following each transfer the top sheet of 3 MM is removed and the dish is covered with plastic wrap for storage.

The gel is placed in Southern transfer buffer (0.4M NaOH) 15 min. to 1 hour. The correct size blot is labeled with a laundry pen or pencil along the lower left edge. Labeling includes operator's initials, notebook page number, and date along with such other information as desired. The blotting membrane is wetted with pure water. The blotting platform is flooded thoroughly with blotting solution and the gel is placed face down on the platform, without trapping air between the gel and platform. The gel is flooded thoroughly with blotting solution and immediately the prewetted blotting membrane is placed on the gel by holding it at the two edges and placing the middle of the blot on the gel first. The blot is then slowly lowered onto the gel so that air is not trapped and without shifting the position of the membrane on the gel. The membrane is flooded with blotting solution and a pipette is carefully rolled over the surface two or three times in order to remove any trapped air. The membrane is flooded with blotting solution and two pieces of the corresponding sized 3 MM paper, prewetted in blotting solution, are placed onto the membrane, flooded and the bubbles are rolled out. Two pieces of dry 3 MM paper are placed on the prewetted papers followed by a 2" stack of paper towels. The edge of the gel is carefully sealed with parafilm so that there is no buffer path other than through the gel. A glass plate is placed on top of the paper towels and approximately 1 Kgm weight is added for a 20×20 cm gel. Transfer is complete in 4 hours to overnight.

Following transfer the paper towels and 3MM overlay are discarded. The membrane is removed to a baking dish containing 2×SSC, swirled briefly and the wash solution is discarded. An additional few hundred mls. of wash solution are added and a gloved hand, that has been rinsed to remove any powder that may be present, is used to thoroughly rub the surface of the membrane that was in contact with the gel. The wash solution is poured off, replaced with another portion and the membrane is washed for 15 minutes at room temperature with agitation. After air drying the membrane is dried at 80° C. for 2 hours under vacuum. Membranes may be stored dry at room temperature in plastic wrap or placed immediately into prehybridization solution.

TABLE 1

Reagents For Use in DNA Typing

1. TBI (transport buffer no. 1)(WCLB white cell lysis buffer) 100 mM NaCl, 25 mM EDTA pH8, 10 mM Tris pH 8, 2. TB2 10% SDS filtered through a 0.22 micron filter and autoclaved.

3. TB3 10 mg/ml Proteinase K. PK is suspended in TBI and predigested at 37° C. 30 minutes. Stored frozen for long term at 4° C. for up to one month.

4. Phenol Chloroform reagent (24:24:1 phenol:chloroform:isoamyl alcohol) Crystalline phenol is melted at 60° C. with 1 M Tris 8 and 10 mM EDTA 8. The aqueous layer is twice drawn off and replaced by TE. The TE is checked for pH >8.0 with a pH strip. If pH remains below >8.0 the TE is withdrawn and replaced until the pH is >8.0. 8 hydroxyquinoline is then added to a concentration of 0.1%. The phenol is then stored at 4° C. and used for up to six months.

5. TE. 10mM Tris 8, 1mM EDTA 8

6. Chloroform reagent. One part isoamyl alcohol is added to 24 parts $CHCl_3$.

7. Precipitation salts are 3.3 M NaOAc pH not adjusted.

8. RCLB (red cell lysis buffer) 10 mM NaCl, 10 mM Tris 8, 1 mM EDTA 8.

9. 95% EtOH USP.

10. Ethidium bromide solution. Make up at 10 mg/ml and store in light protected container at 4° C. 11. 50 ×TAE electrophoresis buffer. 2M Tris acetate, 0.1M EDTA. Per liter, dissolve 242.0 gm Tris base in 400 ml DI water. Add 57.1 ml glacial acetic acid (HOAc) and 200 ml 0.5M EDTA pH 8. Bring to 1 l and mix.

12. 500 mM EDTA pH 8. Per liter, add 186.1 gms $Na_2$ $EDTA._2$ $H_2O$ to 800 ml DI water on a magnetic stirrer. Adjust to pH 8 with NaOH pellets, approximately 20 gms. Adjust to 1 l, mix and autoclave.

13. 20 ×SSC. 3M NaCl, 0.3 M Sodium Citrate. Per liter, add 175.5 gm Nacl and 88.5 gm Sodium Citrate dihydrate.

14. 1M $MgCl_2$. Per 100 ml, 20.3 gm $MgCl_2.6H_2O$.

15. 10×HinF I Restriction buffer (BRL React 2). 0.5M Tris pH, 0.1M $MgCl_2$, 0.5M Nacl.

16. 10×spermidine HCl is 40 mM in $H_2O$.

17. Loading buffer is 50% glycerol in 1×Hinf restriction buffer with 0.1% bromphenol blue.

18. Southern Transfer solution. 0.4M NaOH.

I claim:

1. A DNA probe capable of specifically hybridizing to DNA from an allele of the locus, D4S139.

2. The DNA probe of claim 1 wherein said DNA is labeled.

3. The DNA probe of claim 2 wherein said label is selected from the group consisting of radioisotopes, fluorescers, antigens, biotin, fluorochromes and luminescers.

4. A method for determining the existence of a biological relationship, comprising the steps of
   digesting DNA from a biological sample taken from an individual whose biological relationship is questioned and DNA from a biological sample taken from a putative biological relation in parallel with a restriction endonuclease;
   size-fractionating said restriction endonuclease-digested DNA fragments;
   hybridizing said DNA fragments with a labeled DNA probe capable of specifically hybridizing to DNA from alleles of the VNTR locus D4S139;
   separating nonhybridized labeled probe;
   detecting bound labeled probe; and
   analyzing the identity or partial identity of the hybridization patterns of the individual and the putative biological reaction.

5. The method of claim 4 wherein the DNA probe comprises an oligonucleotide having the sequence 5'-GCCGTGTCCTCGGCTCTCAGG-3', or the complement of said sequence.

6. The method of claim 4 wherein said restriction endonuclease is selected from the group consisting of TaqI, EcoRI, HindIII, AluI, HinfI, HaeIII, RsaI, BamHI, BolII, PstI and XbaI.

7. The method of claim 4 wherein said label is selected from the group consisting of radioisotopes, fluorescers, antigens, biotin, fluorochromes and luminescers.

8. The method of claim 4 including, prior to the step of digesting, isolating DNA from the biological sample of the individual and/or putative biological relation.

9. The method of claim 4 including, subsequent to the step of size-fractionating, affixing the size-fractionated DNA fragments to a suitable substrate.

10. The method of claim 9 wherein the substrate is selected from the group consisting of nylon and nitrocellulose.

11. The method of claim 4 wherein the step of hybridizing is conducted under highly stringent conditions.

12. The method of claim 4 wherein the restriction endonuclease-digested DNA samples are size-fractionated in parallel.

13. The method of claim 4 wherein the step of hybridizing is conducted in an agarose gel.

14. The method of claim 13 including, prior to the step of hybridizing, drying the agarose gel.

15. The method of claim 4 wherein said biological sample is a blood sample.

16. A method for the identification of the source of a bio-forensic specimen, comprising the steps of:
   digesting DNA from a bio-forensic specimen and DNA bio-forensic specimen in parallel with a restriction endonuclease;
   size-fractionating said restriction endonuclease-digested DNA fragments;
   hybridizing said DNA fragments with a labeled DNA probe capable of specifically hybridizing to DNA from alleles of the VNTR locus D4S139;
   separating nonhybridized labeled probe;
   detecting bound labeled probe; and
   determining whether the putative source is the actual source of the bio-forensic specimen.

17. The method of claim 16 wherein the DNA probe comprises an oligonucleotide having the sequence 5'-GCCGTCTCCTCGGCTCTCAGG-3', or the complement of said sequence.

18. The method of claim 16 wherein the restriction endonuclease is selected from the group consisting of TagI, EcoRI, HindIII, AluI, HinfI, HaeIII, RsaI, BamHI, BglII, PstI and XbaI.

19. The method of claim 16 wherein the bio-forensic specimen is selected from the group consisting of blood, dried blood, dried bloodstains, dried vaginal fluid stains, semen, dried semen, dried semen stains, oral swabs, vaginal swabs, vaginal fluids, hair root and body tissue.

20. The method of claim 16 wherein said label is selected from the group consisting of radioisotopes, fluorescers, antigens, biotin, fluorochromes and luminescers.

21. The method of claim 16 including, prior to the step of digesting, isolating DNA from the bio-forensic specimen and/or biological sample.

22. The method of claim 16 including, subsequent to the step of size-fractionating, affixing the size-fractionated DNA fragments to a suitable substrate.

23. The method of claim 22 wherein the substrate is selected from the group consisting of nylon and nitrocellulose.

24. The method of claim 16 wherein the step of hybridizing is conducted under stringent conditions.

25. The method of claim 16 wherein the restriction endonuclease-digested DNA samples are size-fractionated in parallel.

26. The method of claim 16 wherein the step of hybridizing is conducted in an agarose gel.

27. The method of claim 26 including, prior to the step of hybridizing, drying the agarose gel.

28. A method for the identification of the haplotype of the source of a biological sample, comprising the steps of:
   digesting DNA from a biological sample with a restriction endonuclease;
   size-fractionating said restriction endonuclease-digested DNA fragments;
   hybridizing said DNA fragments with a labeled probe capable of specifically hybridizing to the DNA from alleles of the VNTR locus D4S139;
   separating nonhybridized labeled probe;
   detecting bound labeled probe; and
   determining the haplotype at the D4S139 locus of the DNA in the biological sample.

29. The method of claim 28 wherein the DNA probe comprises an oligonucleotide having the sequence 5'-GCCGTCTCCTCGGCTCTCAGG-3', or the complement of said sequence.

30. The method of claim including, prior to the step of digesting, isolating DNA from the biological sample.

31. The method of claim 28 including, subsequent to the step of size-fractionating, affixing the size-fractionated DNA fragments to a suitable substrate.

* * * * *

UNITED STATES PATENT AND TRADEMARK OFFICE
CERTIFICATE OF CORRECTION

PATENT NO. : 5,032,501
DATED : July 16, 1991
INVENTOR(S) : Eric C. B. Milner

It is certified that error appears in the above-identified patent and that said Letters Patent is hereby corrected as shown below:

In column 16, claim 6, line 52, please delete "BolII" and substitute therefor -- BglII --.

In column 17, claim 16, line 13, after "DNA" please insert -- from a biological sample taken from a putative source of the --.

In column 17, claim 17, line 27, please delete "GCCGTCTCCTCGGCTCTCAGG-3'" and substitute therefor -- GCCGTGTCCTCGGCTCTCAGG-3' --.

In column 18, claim 29, line 35, please delete "GCCGTCTCCTCGGCTCTCAGG-3'" and substitute therefor -- GCCGTGTCCTCGGCTCTCAGG-3' --.

In colum 18, claim 30, line 37, after "claim " please insert -- 28 --.

Signed and Sealed this

Sixth Day of October, 1992

Attest:

DOUGLAS B. COMER

*Attesting Officer*     *Acting Commissioner of Patents and Trademarks*